United States Patent [19]
Miura

[11] 4,213,349
[45] Jul. 22, 1980

[54] METHOD OF AND APPARATUS FOR MEASURING STIFFNESS

[76] Inventor: Koryo Miura, 3-9-7, Tsurukawa, Machida-Shi, Tokyo-To, Japan

[21] Appl. No.: 869,940

[22] Filed: Jan. 16, 1978

Related U.S. Application Data

[63] Continuation of Ser. No. 754,240, Dec. 27, 1976, abandoned.

[30] Foreign Application Priority Data

Dec. 27, 1976 [JP] Japan ................................ 51-159579

[51] Int. Cl.$^3$ ............................................ G01N 3/20
[52] U.S. Cl. ........................................ 73/847; 73/852
[58] Field of Search ................. 73/849, 851, 852, 853, 73/854, 847, 848

[56] References Cited

U.S. PATENT DOCUMENTS

| | | | |
|---|---|---|---|
| 2,338,338 | 1/1944 | Kieckhefer | 73/854 |
| 3,022,662 | 2/1962 | Hebeler | 73/847 X |
| 3,194,063 | 7/1965 | McKean | 73/852 X |

*Primary Examiner*—Jerry W. Myracle
*Attorney, Agent, or Firm*—Koda and Androlia

[57] ABSTRACT

In a testing machine a test piece and a reference piece having a known spring constant are superposed with fulcrums interposed between the opposite ends thus establishing a mirror image relationship. A load is applied to the center of the assembly by means of an elastic ring thereby creating a definite relative displacement between the test piece and the reference piece and the relative displacement is measured to determine the bending stiffness of the test piece. According to modified embodiments the torsional stiffness and tension can be measured.

9 Claims, 13 Drawing Figures

METHOD OF AND APPARATUS FOR MEASURING STIFFNESS

This is a continuation of application Ser. No. 754,240, filed Dec. 27, 1976, now abandoned.

BACKGROUND OF THE INVENTION

This invention relates to a method and apparatus for measuring the stiffness of materials utilized as structural members or the like.

The bending stiffness, for example, of a test piece of such material is generally obtained by multiplying the Young's modulus of the material and the moment of inertia I of the test piece. With recent development of synthetic materials and such compound structures as sandwich structures, it is the recent trend to express the strength of the material in terms the bending stiffness B instead of troublesome method involving the measurement of the Young's modulus and the calculation of the moment of inertia I.

Heretobefore, the bending stiffness B has been measured by means of an Amsler type universal testing machine. More particularly, taking a typical three point bending mode as an example, the opposite ends of a simple beam 1 are supported on sharp supports or fulcrums 2 and a concentrated load W is applied to the center of the beam 1 as shown in FIG. 1. The relationship between the maximum deflection δ and the bending stiffness B=E·I under these conditions is expressed by the following equation $$\delta = Wl^3/48E \cdot I$$

where l represents the distance or span between the supports. Accordingly, in this testing machine it is necessary to mount the supports 2 on a rigid bed or a surface plate 3 so that the testing machine is not only heavy but also expensive. According to the method of measuring bending stiffness described above, since the bending stiffness B is determined as a function of three independent variables that is deflection δ, weight W and span l it has been impossible to obtain a testing machine providing a direct reading of the bending stiffness.

SUMMARY OF THE INVENTION

It is an object of this invention to provide an improved method and apparatus for measuring the stiffness of a test piece which is not required to use heavy and expensive surface bed which is difficult to install.

Another object of this invention is to provide a method and apparatus capable of displaying the stiffness such as bending stiffness, torsional stiffness or tension only as a function of a displacement.

According to one aspect of this invention there is provided a method of measuring the stiffness of a testpiece comprising the steps of combining an elastic member having a known stiffness, the test piece and a rigid frame by means of fulcrums so as to form a dynamics system, forcing the dynamic system to undergo a definite relative displacement through the fulcrums such that the deformation of the elastic member and that of the test piece will effect with each other, portions of the elastic member of the test piece to undergo a definite relative displacement without varying the linear relation between the load and the displacement of the system and detecting the amount of relative displacement of the elastic member thereby determining the stiffness of the test piece.

According to another aspect of this invention there is provided a method of measuring the torsional stiffness of a test piece comprising the steps of securing one end of an elastic member having a known torsional stiffness and one end of the testpiece to rigid supports with the other ends opposed each other, applying a load on the other ends in the opposite peripheral direction thereby causing the other ends to undergo a definite relative angular displacement, and measuring the angular displacement of the elastic member thereby determining the torsional stiffness of the test piece.

According to another aspect of this invention there is provided a method of measuring the tension of a test piece comprising the steps of combining an elastic member having a known stiffness, the test piece and a rigid supporting frame into a dynamic system such that when the elastic member and the test piece are forced to undergo a definite relative deformation the deformation of the elastic member and the deflection of the test piece will effect with each other and measuring the amount of the relative displacement of the elastic member.

According to another aspect of this invention there is provided apparatus for measuring the stiffness of a test piece comprising a reference member having a known stiffness, a test piece superposed upon the reference member with fulcrums interposed between the opposing ends of the reference member and the test piece, a rigid frame, a support secured to the frame for supporting an intermediate portion of one of the superposed reference member and the test piece, an elastic member having a known stiffness and interposed between corresponding intermediate portion of the other of the superposed reference member and the test piece, means mounted on the frame for applying a force through a fulcrum to a system comprising the elastic member, the reference member and the test piece thereby causing the system to undergo a definite relative displacement, and means for detecting the relative displacement of the elastic member.

According to a further aspect of this invention there is provided apparatus for measuring the tension of a test piece comprising a spring, cam means for applying a definite axial displacement to one end of the spring, means for urging the other end of the spring against the test piece in a direction perpendicular to the surface thereof and means for detecting the axial displacement of the coil.

According to still further aspect of this invention, there is provided apparatus for measuring the torsional stiffness of a test piece, comprising a rigid support to rigidly support one ends of a reference piece having a known torsional stiffness and one end of the test piece with the other ends opposed to each other, means for applying twisting forces to the other ends in opposite directions, thereby creating a relative angular displacement between said other ends, and means for detecting said relative angular displacement.

BRIEF DESCRIPTION OF THE DRAWINGS

Further objects and advantages can be more fully understood from the following detailed description taken in conjunction with the accompanying drawings in which.

DESCRIPTION OF THE PREFERRED EMBODIMENT

Figure 1:
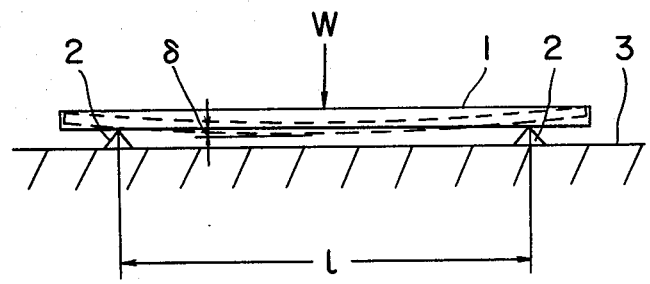
FIG. 1 is a diagrammatic representation for explaining a prior art method of measuring bending stiffness.
Figure 2:
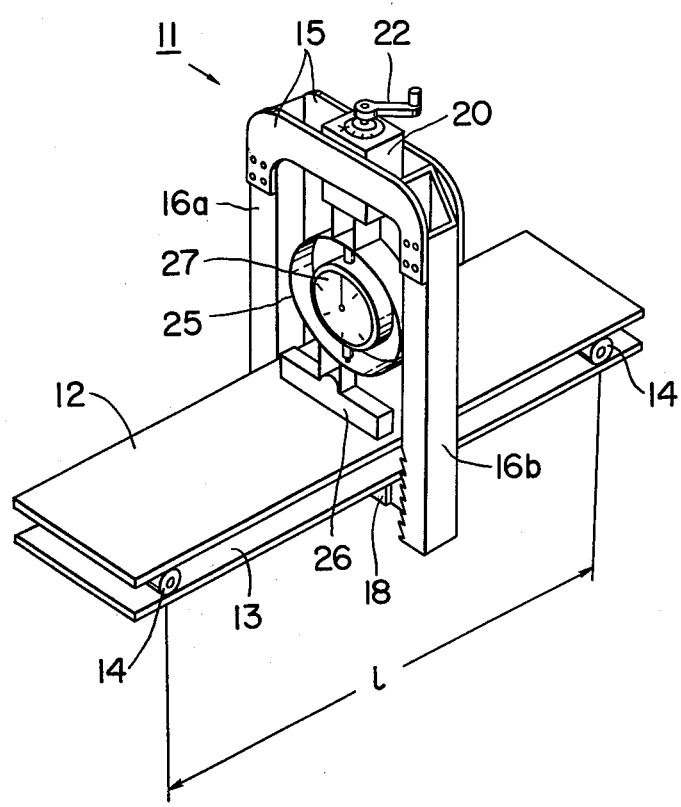
FIG. 2 is a perspective view of a testing machine of this invention for measuring bending stiffness.
Figure 3:
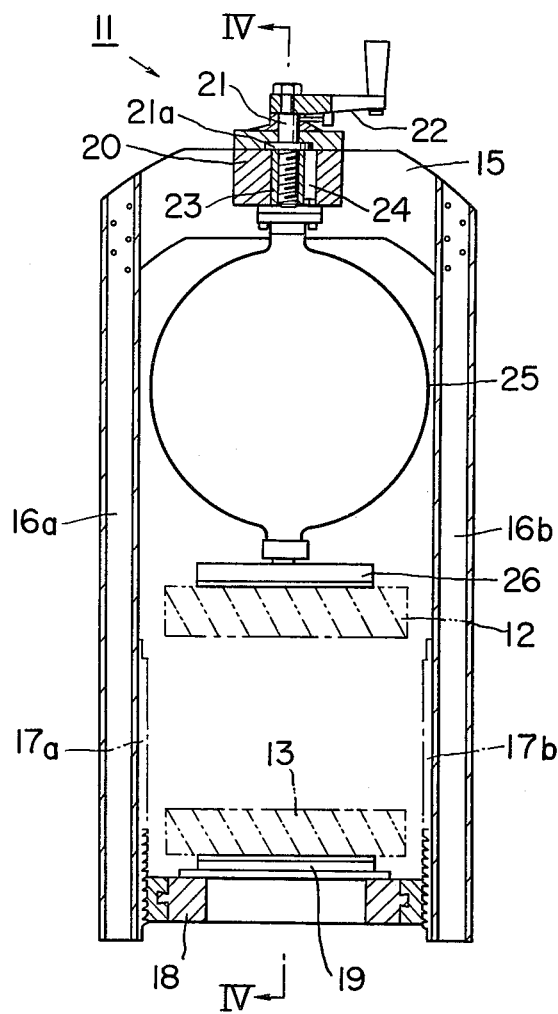
FIG. 3 is a vertical sectional view of the testing machine shown in FIG. 2.
Figure 4:
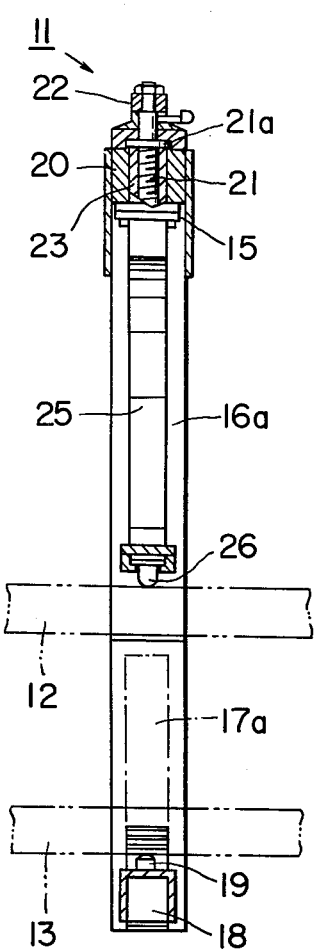
FIG. 4 is a sectional view of the testing machine shown in FIG. 3 taken along a line IV—IV.
Figure 5:
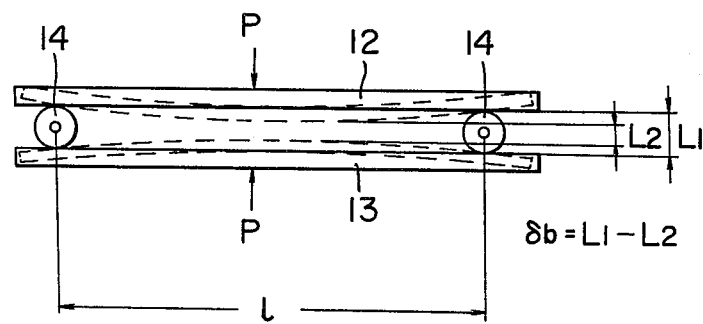
FIG. 5 is a diagrammatic side view of a test piece and a reference piece showing the defection thereof when a test load is applied.
Figure 9:
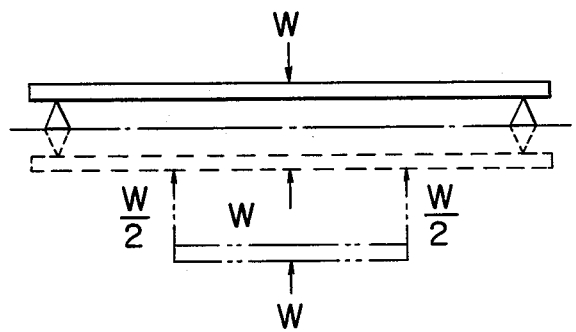
FIG. 9 is a diagram for explaining the mirror image relationship.

Referring now to FIGS. 2 to 4 of the accompanying drawing, the opposite ends of a test piece 12 is mounted on spaced supports 14 and a reference piece 13 having a known spring constant $K_{o2}$ or bending stiffness is placed beneath the supports 14 in a mirror image relationship with respect to the test piece 12. The term "mirror image relationship" is used herein to mean that a dynamics system supported by fulcrums and shown by solid lines and an identical dynamics system shown by dotted lines are supported to oppose with each other in a relation of an object and an image thereof as shown in FIG. 9. When arranged in this manner both dynamic systems of the test piece and reference piece operate as if there were a surface plate having an infinitely large stiffness on the boarder line therebetween. Of course, in the mirror image relationship described above, the added dynamics system (shown by dotted lines) is not always required to be perfectly identical to the original dynamics system (shown by solid lines), provided that the added dynamics system applies to the original dynamic system the same reaction as the surface plate. In other words, the test piece and the reference piece may have different bending stiffnesses, and divided loads as shown by dot and dash lines may be applied on the added dynamics system. Theoretically, the fulcrums 14 should have knife edges on their upper and lower sides, but thick cylinders or round rods are sufficient for practical machines. To construct the testing machine as a direct reading type, it is necessary to determine the distance l between the fulcrums 4, that is the span of the test piece 12 (see FIG. 5) to a specific value, for example 1000 mm and to measure the spring constant $K_{o2}$ under this condition.

As best shown in FIGS. 3 and 4 the bending moment testing machine 11 embodying the invention comprises a pair of rigid vertical pipes or legs 16a and 16b connected to the opposite sides of a connecting yoke 15. These pipes 16a and 16b are required to act as rigid bodies against compressive and tension loads acting in the direction of length and to have a small weight as far as possible for easy handling. On their confronting inner surfaces at the lower ends, these rigid pipes are provided with racks 17a and 17b between which is positioned a crossbar 18 so that the position thereof may be varied according to the spacing between the test piece 12 and the reference piece 13. A knife edge 19 is secured on the upper surface of the crossbar for engaging the lower surface of the reference piece 13.

At the center of the yoke 15 is secured a bearing 20 for receiving a feed screw 21 having a thrust collar 21a and an operating handle 22. A sleeve 23 is fitted over the feed screw 21 to be movable in the axial direction by a key 24 interposed between the sleeve and bearing. The feed screw 21 holds the upper end of an elastic member in the form of an elastic ring 25 provided with a knife edge 26 at its lower end which cooperates with said knife edge 19 to cause the reference piece 13 and the test piece 12 to displace by $\delta t$. Of course, the spring constant $K_d$ of the elastic ring 25 is to be measured beforehand and a precise displacement meter such as a dial gauge 27 or a differential transformer, for example, is provided as shown in FIG. 2.

According to this invention, the bending stiffness B of the test piece 12 is measured by the testing machine 11 described above according to the following procedures. More particularly, the test piece 12 and the reference piece 13 are positioned in the testing machine 11 such that they are clamped between the knife edges 19 and 26, and then the handle 22 is rotated to apply a definite displacement, that is a forced relative displacement of a definite value $\delta t$, to the sleeve 23 thereby applying a predetermined load P upon the elastic ring and the reference piece. As a consequence, these pieces deform as shown by dotted lines in FIG. 5 thereby creating a flexure $\delta b = L_1 - L_2$ between them, where $L_1$ represents the spacing between the pieces 12 and 13 before flexure and $L_2$ the spacing after flexure. At the same time, the elastic ring 25 is caused to flex by $\delta d$ by the displacement of the sleeve 23.

Figure 6:
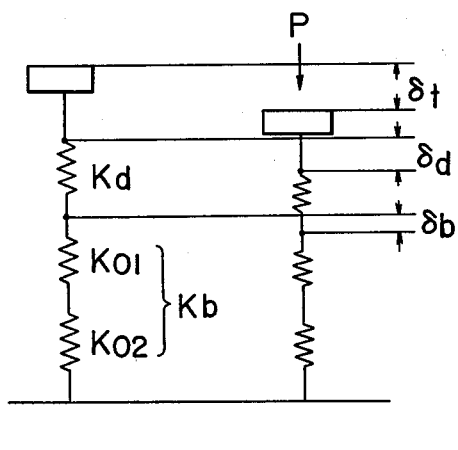
FIG. 6 is an equivalent system of the testing machine shown in FIGS. 2 and 3.

FIG. 6 is an equivalent diagram of respective elements showing the states thereof before and after deformation. The bending or flexural stiffness of the test piece 12 can be calculated as follows from this figure.

Thus, in FIG. 6, the following equations can be derived out from the displacement $\delta t$ of the sleeve 23 and the flexures of respective elements 12, 13 and 25

$$K_d = P/\delta_d \tag{1}$$

$$K_b = P/\delta b \tag{2}$$

$$\delta_t = \delta_d + \delta_b \tag{3}$$

By solving these simultaneous equations it is possible to obtain the compound spring constant $K_b$ of the test piece 12 and the reference piece 13.

$$K_b = \frac{P}{\delta_t - \delta_d} = \frac{\delta_d \cdot K_d}{(\delta_t - \delta_d)} \tag{4}$$

As is well known in the art, there is the following relationship among the compound spring constant $K_b$, the spring constant $K_{o2}$ of the reference piece 13 and that of the test piece 12.

$$\frac{1}{K_b} = \frac{1}{K_{01}} + \frac{1}{K_{02}} \tag{5}$$

From equation (5) the spring constant $K_{o1}$ of the test piece can be determined as follows.

$$K_{01} = \frac{K_b K_{02}}{K_{02} - K_b} \quad (6)$$

The relationship between the spring constant $K_{o1}$ and the bending stiffness B can be obtained in the following manner. Thus, when a concentrated load W is applied to the central portion of a beam supported at its opposite ends, the flexure $\delta$ is expressed by a general equation $$\delta = Wl^3/48EI \quad (7)$$

By applying this relationship to the test piece 12 we obtain $$K_{01} = \frac{P}{\delta_{01}} = \frac{48(EI)}{l^3} \quad (8)$$

By modifying equation (8), the bending stiffness B is shown by an equation $$B = (EI)_{01} = \frac{l^3}{48} K_{01} \quad (9)$$

By sequentially substituting equations 6 and 4 into equation 9, we obtain $$B = (EI)_{01} = \frac{l^3}{48} \cdot \frac{\delta_d \cdot K_d \cdot \frac{X}{Y} \cdot K_{02}}{K_{02} \cdot \delta_b - \delta_d \cdot K_d \cdot \frac{X}{Y}} = \frac{l^3}{48} \cdot \frac{K^2 \cdot K_d \cdot K_{02} \cdot \delta_d}{\{\delta_t(X+Y) - \delta_d \cdot Y\} \cdot K_{02} \cdot Y - \delta_d \cdot K_d \cdot X^2}$$

In equation 10 since the values of $K_{o2}$, $K_d$ and $\delta_t$ are known, by specifying the span l as a reference dimension, it can be noted that the bending stiffness B can be displayed merely as a function of $\delta_d$, that is the reading of the dial gauge 27. In other words, where a value $$\frac{l^3}{48} \cdot \frac{\delta_d \cdot K_d \cdot K_{02}}{K_{02}(\delta_t - \delta_d) - K_d \cdot \delta_2}$$

is marked at a position corresponding to the displacement $\delta_d$ of the pointer of the dial gauge 27 it is possible to directly determine the value of the bending stiffness B.

In a special case wherein the test piece 12 is identical to the reference piece B, equation 5 is modified as follows $$1/K_b = 2/K_{o1} \quad (5a)$$

Consequently, equation 10 becomes $$B = (EI)_{01} = \frac{l^3}{24} \cdot \frac{\delta_d \cdot K_d}{\delta_t - \delta_d}$$

In another case wherein the bending stiffness of the reference piece is infinitely larger than that of the test piece, equation 5 becomes $$1/K_b = 1/K_{o1} \quad (5b)$$

and equation 10 becomes $$B = (EI)_{01} = \frac{l^3}{48} \cdot \frac{\delta_d K_d}{\delta_t - \delta_d}$$

Thus, in each case the bending stiffness B can be shown as a function of the flexure $\delta_d$ of the elastic ring 25.

Although in the foregoing embodiment, the test piece 12, reference piece 13 and elastic ring 25 were shown cascade connected, it will be clear that the invention is not limited to such particular arrangement but any other arrangement can also be used provided that displacement of the elastic member illustrated as the elastic ring 25 is coupled with the definite displacement of the testpiece and the reference piece which are arranged in a mirror image relationship. Further, the elastic member is not limited to a ring but may be any member having a desired spring constant sufficient to drive the displacement meter in accordance with the displacement or deflection of the elastic member such as a flat ring, a leaf spring, and a coil spring. Instead of using a single ring shaped member it is possible to use a plurality of ring shaped members which are connected in cascade. In this case, the flexure of one or more ring shaped members, or a portion of one member can be used to actuate the displacement member. The elastic member and the test piece are combined such that when the load is applied to cause a definite relative displacement the linear relation between the load and the displacement of the system would not be changed.

Figure 7:
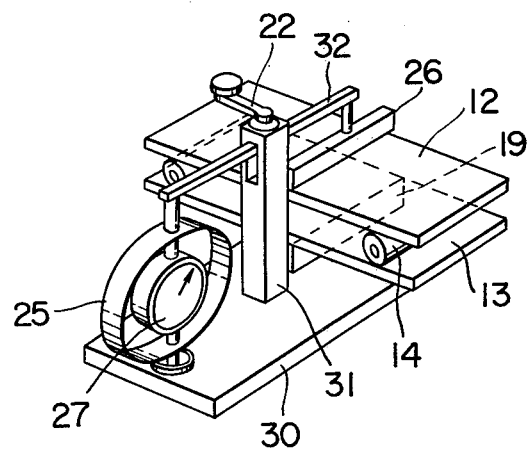
FIG. 7 is a perspective view showing a modified embodiment of this invention.
Figure 8:
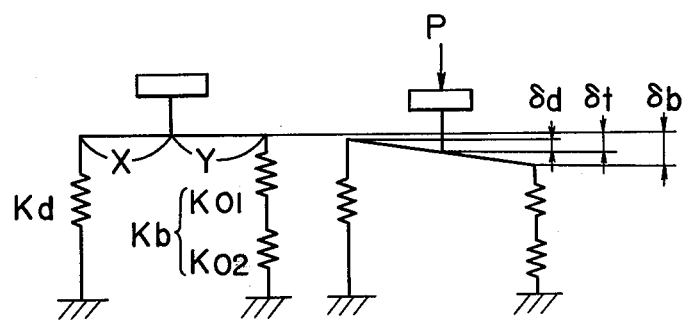
FIG. 8 is an equivalent system of the modified embodiment shown in FIG. 7.

FIG. 7 shows a modified embodiment of this invention in which the elements corresponding to those shown in FIG. 2 are designated by the same reference numerals. This modification is different from FIG. 2 in that a definite displacement is imparted to the test piece 12 and the reference piece 13 by the elastic member 25 through a lever 32 pivotally supported by a upright post 31 on the bed 30. An equivalent system of this modification is shown in FIG. 8. Thus, by the operation of handle 22, a definite displacement $\delta_t$ is applied to the fulcrum of the lever 32 thereby causing the load P to the fulcrum. Consequently, by denoting the lengths of the left and right-hand sides of the lever 32 by X and Y respectively as shown in FIG. 8, the following relationships hold.

$$P = \delta_d \cdot K_d + \delta_b \cdot K_b \quad (11)$$

$$P = \frac{1}{Y}(X+Y)\delta_d \cdot K_d \quad (12)$$

$$\delta_t = \frac{\delta_b \cdot A + \delta_d \cdot Y}{X+Y} \quad (13)$$

From equations 11 and 12, we obtain $$K_b = \frac{\delta_d \cdot K_d \cdot \frac{X}{Y}}{\delta_b} \quad (14)$$

In the same manner as equation 10 described in connection with FIG. 6 the bending stiffness B can be calculated according to the following equation 15.

$$B = (EI)_{01} = \frac{l^3}{48} \cdot \frac{K_b \cdot K_{02}}{K_{02} - K_b} \quad (15)$$

On the other hand, $\delta_b$ can be determined by equation 13, thus $$\delta_d = \frac{\delta_t(X + Y) - \delta_d \cdot Y}{X} \quad (16)$$

By sequentially substituting equations 14 and 16 into equation 15, we obtain $$B = (EI)_{01} = \frac{l^3}{48} \cdot \frac{\delta_d \cdot K_d \cdot \frac{X}{Y} \cdot K_{02}}{K_{02} \cdot \delta_b - \delta_d \cdot K_d \cdot \frac{X}{Y}} =$$

$$\frac{l^3}{48} \cdot \frac{X^2 \cdot K_d \cdot K_{02} \cdot \delta_d}{\{\delta_t(X + Y) - \delta_d \cdot Y\} K_{02} \cdot Y - \delta_d \cdot K_d \cdot X^2}$$

In the same manner as equation 10, since the values of X, Y, $K_{o2}$ and $\delta_t$ in equation 17 are known it is possible to express the bending stiffness B as a function of the deflection $\delta_d$ of the elastic ring 25 by using the span 1 as a reference value. In this example, no reference piece is used.

Although in the foregoing embodiments, a feed screw was used as a means for imparting a definite displacement $\delta_t$ it will be clear that a rack or a hydraulic pressure actuator may be substituted for the feed screw.

Figure 10:
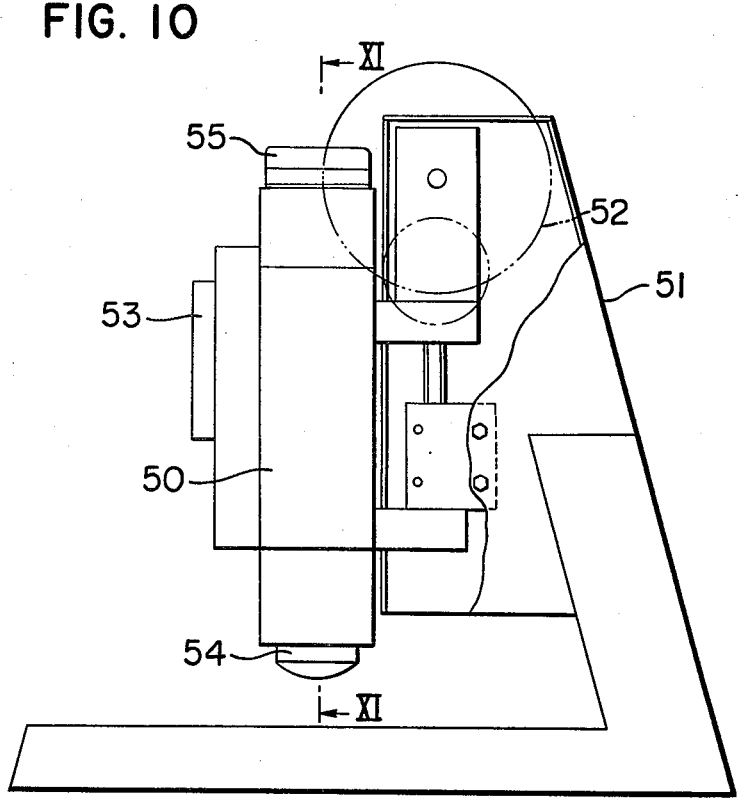
FIG. 10 is a side view showing still further modification of the testing machine.
Figure 11:
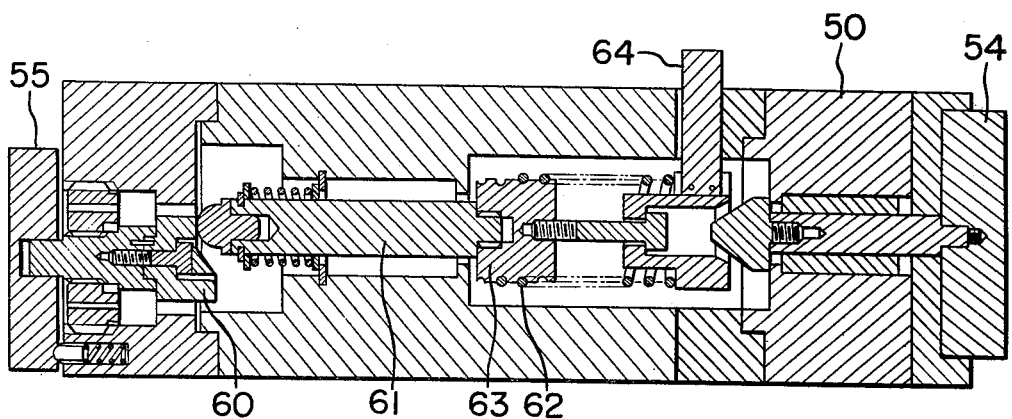
FIG. 11 is a sectional view of the measuring box of the testing machine shown in FIG. 10 taken along a line XI—XI.

Still another embodiment of this invention is shown in FIGS. 10 and 11 and comprises measuring box 50 adjustably mounted on a L shaped support 51. The measuring box is provided with a zero point adjuster 52, a dial gauge 53, an attachment 54 adapted to apply a load to a test price, in this case a racket gut which is mounted on the base of the support 51 so as to be urged against attachment 54. The configuration of the attachment is changed according to the contour of the test piece.

As shown in FIG. 11, the measuring box 50 comprises a cam 60 rotated by a handle 55 or a knob. As the cam is rotated, a rod 61 is reciprocated to compress or release a coil spring 62. The spring constant of the coil spring 63 is adjusted by a threaded member 63. It will be noted that the coil spring 62 of this embodiment corresponds to the elastic ring 25 shown in FIG. 2. The displacement of the attachment 54 is transmitted to a dial gauge or other mechanical or electronic displacement meter, not shown, through a lever 64. In operation, the test piece (not shown) is urged against the attachment 54 by adjusting the position of the measuring box until the attachment is operatively connected to the coil spring. Then the cam is rotated to deform the test piece.

Figure 12:
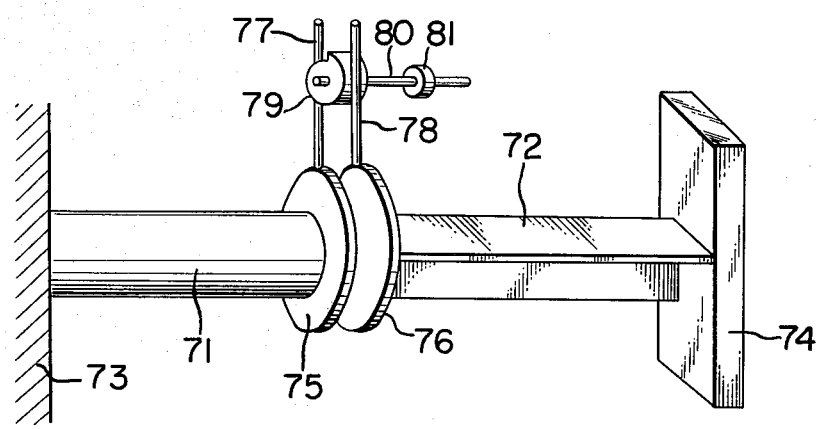
FIGS. 12 and 13 are diagrammatic representations of another embodiment of this invention utilized to measure torsion stiffness.
Figure 13:
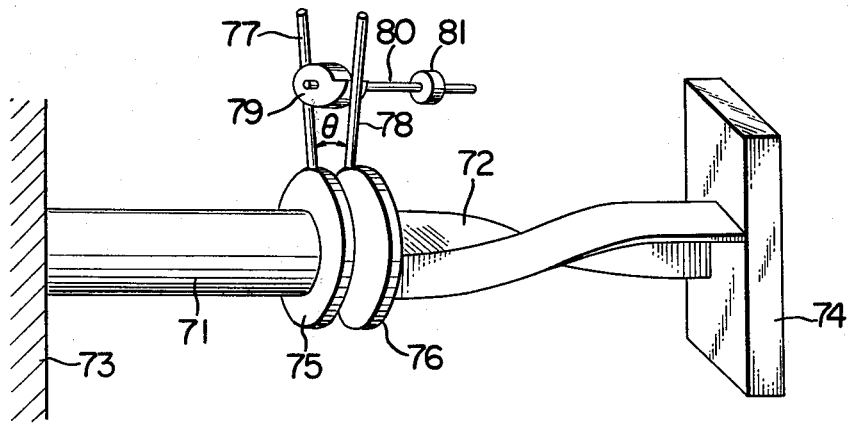

FIGS. 12 and 13 show still another embodiment of this invention suitable to measure the torsion stiffness of a structural member for example an angle member. A reference member shown as a circular rod 71 and having a known torsion stiffness is secured at one end to a rigid support 73 and a circular disc 75 is secured to the other end of the rod 71. One end of a test piece shown as an angle member 72 is secured to the other rigid support 74 and a circular disc 76 is secured to the other end of the sample member to oppose the disc 75. Operating arms 77 and 78 are secured to spaced points of the peripheries of the discs 75 and 77 and a rotary cam 79 is interposed between the arms. When the cam 79 is rotated by shaft 80 both members 71 and 72 are twisted. Thus, by detecting the relative angular displacement $\theta$ between the arms 77 and 78, the torsion stiffness of the test piece can be measured. To measure the relative angular displacement $\theta$, any one of well known mechanical or electrical device 81 may be used.

As can be noted from the foregoing description, the invention provides a compact and light weight direct reading type testing machine which is not required to use heavy and rigid surface plate yet can readily measure the stiffness of various materials without knowing the test load. Since the testing machine of this invention is handy and transportable it is possible to readily apply it to a body to be measured irrespective of its position and shape. For example, it is possible to measure the bending stiffness of a pipe line of a chemical plant without dismounting the pipe line.

Moreover, the accuracy of the measurement is extremely high. When considering the characteristics of a structural member in terms of the strain, so long as the spring constant is measured the result is correct. However, since conversion of the spring constant into the bending stiffness is relied upon the theory of a pure beam not considering a term introduced by shear deformation, an error up to about 1% is inevitable. In contrast, according to this invention, only the displacement of the test piece is detected the accuracy of the measurement can be improved by increasing the working accuracy of the component parts of the testing machine. A practical design of the measuring box is shown in FIG. 11. As shown, the measuring box is compact and comprises a relatively small number of elements of simple design. Consequently, accurate machining and assembly of these elements is easy.

I claim:

1. A method of measuring the stiffness of a test piece comprising the steps of combining an elastic member having a known stiffness, said test piece, and a rigid frame by means of fulcrums in a mirror image relationship so as to form a dynamics system, forcing said dynamics system to undergo a definite relative displacement through said fulcrums such that the deformation of said elastic member and that of said test piece will effect with each other without varying the linear relation between the load and the displacement of said system, and detecting the amount of relative displacement of said elastic member thereby determining the stiffness of said test piece.

2. A method of measuring the stiffness of a test piece comprising the steps of combining an elastic member having a known system comprising a beam having a known bending stiffness, said test piece and a rigid frame by means of fulcrums so as to form a dynamic system wherein said elastic member and said test piece are combined in a mirror image relationship, forcing said dynamic system to undergo a definite relative displacement through said fulcrum such that deformation of said elastic member and that of said test piece will effect with each other without varying the linear relations between the load and the displacement of said system, and detecting the amount of relative displacement of said elastic member whereby the bending stiffness of said test piece is determined.

3. A method of measuring the torsional stiffness of a test piece comprising the steps of securing one end of an elastic member having a known torsional stiffness and one end of the test piece to rigid supports with the other ends opposed each other, applying a load on said other ends in the opposite peripheral directions thereby causing said other ends to undergo a definite relative angular displacement, and measuring the angular displacement of said elastic member thereby determining the torsional stiffness of said test piece.

4. Apparatus for measuring the stiffness of a test piece comprising a reference member having a known stiffness, a test piece superposed upon said reference member with fulcrums interposed between the opposing ends of said reference member and said test piece, a rigid frame, a support secured to said frame for supporting an intermediate portion of one of the superposed reference member and the test piece, an elastic member having a known stiffness and interposed between corresponding intermediate portion of the other of said superposed reference member and said test piece, means mounted on said frame for applying a force through a fulcrum to a system comprising said elastic member, said reference member and said test piece thereby causing said system to undergo a definite relative displacement, and means for detecting said relative displacement of said elastic member.

5. The apparatus according to claim 4 wherein said reference member, said test piece and said fulcrums are combined in a mirror image relationship thereby measuring the bending stiffness of said test piece.

6. The apparatus according to claim 4 wherein said frame comprises an inverted U shaped structure including a pair of legs and a yoke interconnecting said legs, said support is connected between said legs, and said force applying means is supported by said yoke.

7. The apparatus according to claim 4 wherein said elastic member comprises an elastic ring.

8. The apparatus according to claim 4 wherein said elastic member comprises an elastic ring which is connected to a load applying member through a pivoted lever, and said force applying member is urged against said intermediate portion.

9. Apparatus for measuring the torsional stiffness of a test piece comprising a rigid support to rigidly support one end of a reference piece having a known torsional stiffness and one end of said test piece with the other ends opposed each other, means for applying twisting forces to said other ends in opposite directions thereby creating a relative angular displacement between said other ends, and means for detecting said relative angular displacement.

* * * * *